United States Patent [19]

Clémence et al.

[11] Patent Number: 4,975,427
[45] Date of Patent: Dec. 4, 1990

[54] 17-SULFUR-20,21-DINOR-EBURNAMENINES

[75] Inventors: Francois Clémence, Paris; Jean-Luc Haesslein, Rosny Sous Bois; Claude Oberlander, Paris, all of France

[73] Assignee: Roussel Uclaf, Paris, France

[21] Appl. No.: 415,196

[22] Filed: Sep. 29, 1989

[30] Foreign Application Priority Data

Oct. 6, 1988 [FR] France .................. 88 13107

[51] Int. Cl.$^5$ .................. A61K 31/45; C07D 513/14
[52] U.S. Cl. .................. 514/224.5; 544/14
[58] Field of Search .................. 514/224.5; 544/14

[56] References Cited
U.S. PATENT DOCUMENTS
4,218,453  8/1980  Hannart .................. 546/66

Primary Examiner—John M. Ford
Attorney, Agent, or Firm—Bierman and Muserlian

[57] ABSTRACT

A compound selected from the group consisting of a compound of the formula

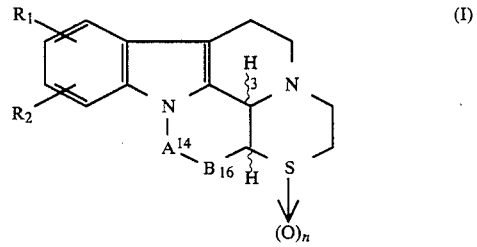

wherein $R_1$ and $R_2$ are individually selected from the group consisting of hydrogen, halogen, alkyl and alkoxy of 1 to 5 carbon atoms, hydroxy, trifluoromethyl and nitro, n is 0,1 or 2 and the group:

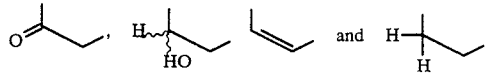

is selected from the group consisting of in all possible racemic or optically active isomer forms and their non-toxic, pharmaceutically acceptable acid addition salts having analgesic, anti-anoxic and anti-ischemic neuronal protective properties.

10 Claims, No Drawings

17-SULFUR-20,21-DINOR-EBURNAMENINES

STATE OF THE ART

U.S. Pat. No. 4,218,453 discloses related compounds.

OBJECTS OF THE INVENTION

It is an object of the invention to provide the novel compounds of formula I and a process and novel intermediates for their preparation.

It is another object of the invention to provide novel analgesic compositions and a novel method of relieving pain in warm-blooded animals.

These and other objects and advantages of the invention will become obvious from the following detailed description.

THE INVENTION

The novel compounds of the invention are selected from the group consisting of a compound of the formula

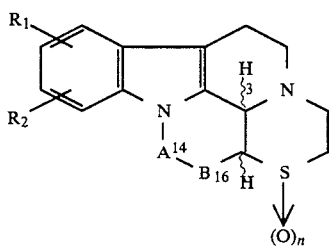

wherein $R_1$ and $R_2$ are individually selected from the group consisting of hydrogen, halogen, alkyl and alkoxy of 1 to 5 carbon atoms, hydroxy, trifluoromethyl and nitro, n is 0,1 or 2 and the group:

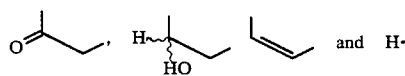 is selected from the group consisting of

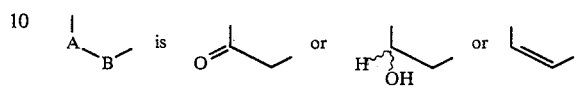

in all possible racemic or optically active isomer forms and their non-toxic, pharmaceutically acceptable acid addition salts.

The 3- and 16-hydrogens in the compounds of formula I may each be of α or β configuration which determines the cis and trans diastereoisomers. The 14-hydroxy may also be in the α or β form.

Examples of $R_1$ and $R_2$ as alkyl or alkoxy are n-butyl, isobutyl, n-pentyl or preferably methyl, ethyl, n-propyl, isopropyl and propoxy, isopropoxy, n-butoxy, sec.-butoxy, tert-butoxy but preferably methoxy and ethoxy. When $R_1$ and $R_2$ are halogen, they may be fluorine, bromine or iodine but preferably chlorine.

Examples of suitable acids for the formation of the nontoxic, pharmaceutically acceptable acid addition salts are inorganic acids such as hydrochloric acid, hydrobromic acid, hydriodic acid, nitric acid, sulfuric acid and phosphoric acid and organic acids such as propionic acid, acetic acid, formic acid, benzoic acid, maleic acid, fumaric acid, succinic acid, tartaric acid, citric acid, oxalic acid, glyoxylic acid, aspartic acid and ascorbic acid, alkanemonosulfonic acids such as methanesulfonic acid, ethanesulfonic acid, propanesulfonic acid, alkanedisulfonic acids such as methanedisulfonic acid, ethanedisulfonic acid, arylmonosulfonic acids such as benzenesulfonic acid and aryldisulfonic acids Among the preferred compounds of formula I are those wherein $R_1$ and $R_2$ are both hydrogen and those wherein

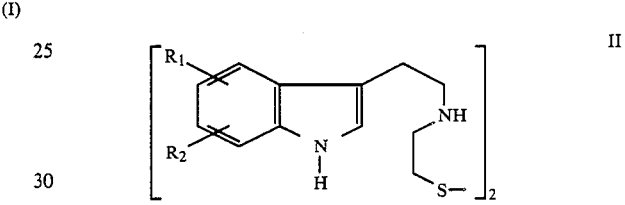

and their non-toxic, pharmaceutically acceptable acid addition salts. Specific preferred compounds are (±) 20,21-dinor-17-thia eburnamenine-14(15H)-one and its acid addition salts, especially fumarate and (14α,16α) (±) 14,15-dihydro-20,21-dinor-17-thia eburnamenine-14-ol.

The novel process for the preparation of the compounds of formula I comprises reacting a compound of the formula

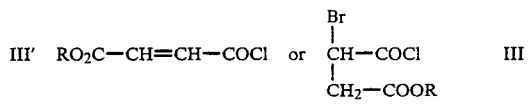

wherein $R_1$ and $R_2$ have the above definitions with an acid chloride of the formula $$\text{III}' \quad RO_2C\text{—}CH\text{=}CH\text{—}COCl \quad \text{or} \quad \underset{\underset{CH_2\text{—}COOR}{|}}{\overset{\overset{Br}{|}}{CH}}\text{—}COCl \quad \text{III}$$

wherein R is alkyl of 1 to 2 carbon atoms to obtain a compound of the formula

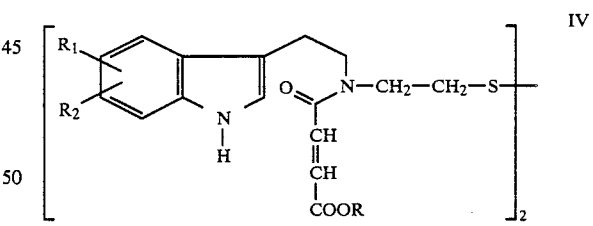

reacting the latter with a reducing agent to obtain a compound of the formula

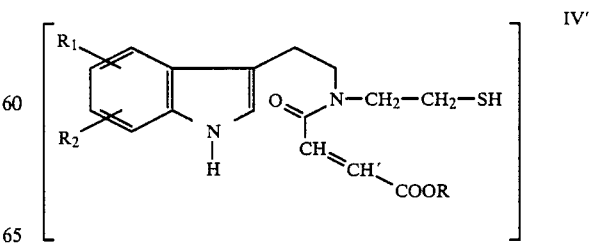

which cyclizes spontaneously into a compound of the formula

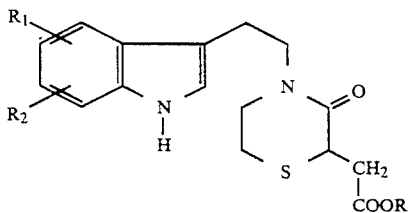

cyclizing the compound of formula V to form the salt of the formula

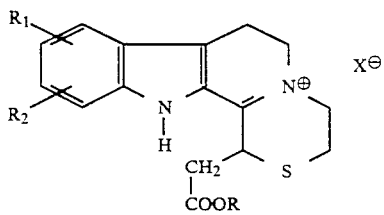

wherein X⁻ is a counter-ion and either reducing the salt of formula VI to obtain a compound of the formula VII in which the two hydrogens are in cis position

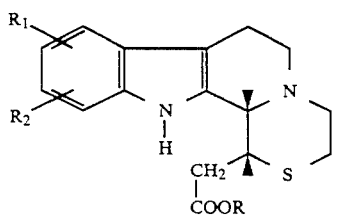

which product of formula VII is cyclized in a basic medium to obtain a compound of formula I in which

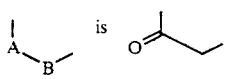

the 3- and 16-hydrogen atoms are in cis position with respect to each other, and n is equal to 0; or the salt of formula VI is cyclized to form a compound of the formula

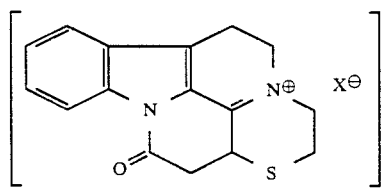

which compound is reduced to obtain a compound of formula I in which

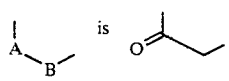

the 3- and 16-hydrogen atoms are in trans position with respect to each other and n is equal to 0 and the said products of formula I may be, if desired, reduced either into the corresponding compounds of formula I in which

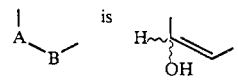

and n is equal to 0 or into compounds of formula I in which

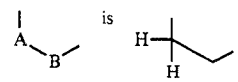

and n is equal to 0 and in that, if desired, the compounds of formula I are dehydrated to obtain the compounds of formula ($I_{D1}$) and ($I_{D2}$) representing the compounds of formula I in which

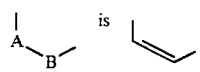

and n is equal to 0, and in that, if desired, the compounds of formula I are submitted to the action of an oxidation agent to obtain the corresponding compounds in which n represents 1 or 2 and they can be salified with an acid.

In a preferred mode of the process, the R of the compound of formula III is methyl and the reaction is effected in the presence of a base such as potassium carbonate, sodium hydroxide or potassium hydroxide and a phase transfer agent such as tetrabutylammonium bromide or hydrogen sulfate the reduction of the disulfide of formula IV is preferably effected with triphenylphosphine in the presence of a monoglyme-water mixture or a mixture of water and dioxane or diglyme or tetrahydrofuran. The cyclization of the compound of formula V is preferably effected with phosphorus oxychloride and X⁻ is therefor a chloride ion.

The reduction of the compounds of formula VI is preferably effected with sodium borohydride in the presence of methanol and the cyclization of a compound of formula VII in a basic medium is preferably effected with an alcoholate-alcohol mixture such as ethanol-sodium ethylate or methanol-sodium methylate. The cyclization of a compound of formula VI into a compound of formula VIII is preferably effected with hydrochloric acid and the reduction of the compound of formula VIII is preferably effected with sodium borohydride in the presence of acetic acid. The reduction of the compounds of formula I is effected with a hydride or mixed hydride such as lithium aluminum hydride, sodium aluminum diethylhydride, diisobutyl aluminum hydride or sodium borohydride at 0° C. or room temperature depending on the desired compound.

The dehydration of a compound of formula I wherein

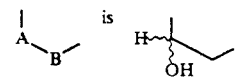

to a compound wherein

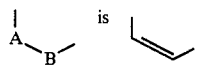

is effected with an acid such as hydrochloric acid, hydrobromic acid, sulfuric acid, acetic acid, p-toluene sulfonic acid or methanesulfonic acid in catalytic amounts. The oxidation of compounds of formula I wherein n is 0 to those wherein n is 1 or 2 is preferably effected with m-chloroperbenzoic acid, magnesium monoperphthalate or sodium periodate. The optically active forms of formula I may be resolved by the usual methods.

In a variation of the process of the invention, the compounds of formula I wherein

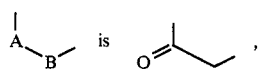

n is 0 and the 3- and 16-hydrogens are trans are oxidized to form the compounds of claim 1 wherein n is 1 or 2 which compounds can be reduced to form compounds of formula I wherein n is 1 or 2 and

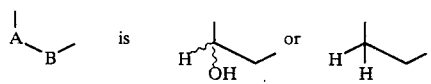

and the compounds of formula I wherein

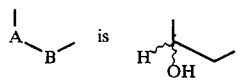

may be dehydrated to form a compound of formula I wherein n is 1 or 2 and

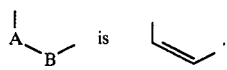

In this variation, the reactants to effect the various transformation are the same as discussed above.

The novel analgesic compositions of the invention are comprised of an analgesically effective amount of at least one compound of formula I and its non-toxic, pharmaceutically acceptable acid addition salts and an inert pharmaceutical carrier or excipient. The compositions may be in the form tablets, dragees, gelules, granules, suppositories, ointments, creams, gels, injectable solutions or suspensions and aerosols.

Examples of suitable excipients are talc, gum arabic, magnesium stearate, starch, cocoa butter, aqueous and non-aqueous vehicles, fatty substances of animal or vegetable origin, paraffin derivatives, glycols, various wetting, dispersing or emulsifying agents and preservatives.

The compounds possess, beside analgesic activity, anti-anoxic and anti-ischemic neuronal protective activity. Certain of the compounds also have useful nootropic properties (anti-amnesic effect and reversion of an amnesic deficiency after a lesion of the septal cholinergic), anti-depressants, neuronal protectors, anti-anoxic, anti-ischemic.

The compositions are useful for the treatment of muscular, articular or nervous pains, dental pains, migraines, shingles and also as complementary treatments in infectious or febrile states. They can also be used in the treatment of cerebral insufficiencies of anoxic or ischemic origin, disorders of memory and attention as well as anti-depressants.

The novel method of the invention for relieving pain in warm-blooded animals comprises administering to warm-blooded animals an analgesically effective amount of at least one compound of formula I and its non-toxic, pharmaceutically acceptable acid addition salts. The compounds may be administered orally, rectally, parenterally or topically to skin and mucous membranes. The usual daily effective amount is to 0.13 to 26.6 mg/kg, depending on the specific compound, method of treatment and condition treated.

The compounds of formulae IV, IV', V, VI, VII and VIII are novel intermediates and are an object of the invention.

Some of the starting compounds of formula II are known from Chemical Abstracts, Vol. 92, 128, 821. Those that are not known may be prepared by reacting chloroacetyl chloride with a compound of the formula

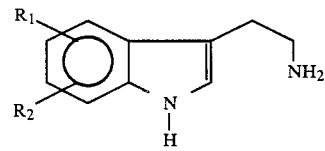

wherein $R_1$ and $R_2$ have the above definition to obtain a compound of the formula

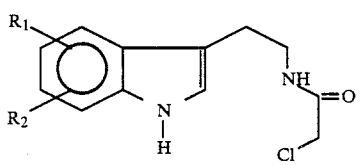

reacting the latter with sodium thiosulfate to obtain a compound of the formula

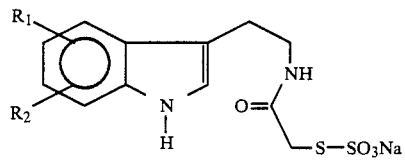

which is reduced by lithium aluminum hydride to the compound of formula II.

Certain of the products of formula (D) are known; for example Chemical Abstracts Vol. 80, 82567. Certain products of formula (C) are also known (see following publications):
Tetrah. Lett 1975 (39) 3399–402
Chem. Pharm. Bull. 28(3), 900–9 (1980)
Tetrah. Lett. 26(37), 4443–6 (1985)
J. Med. Chem. 12(4) 636.8 (1969)
Izv. Akad. Nauk. Arm. SSR 14, 603, 10 (1961)
Yakugaku Zasshi 81, 636–9 (1961)

Rev. Chim. (Bucharest) 19(8) 444–7 (1968)
Khim. Geterotsikl. Soedin. (11) 1505-11 (1973)
J. Pharm. Pharmacol. 31(6) 371-4 (1979).

In the following examples thee are described several preferred embodiments to illustrate the invention. However, it should be understood that the invention is not intended to be limited to the specific embodiments.

EXAMPLE 1

(±)-20,21-dinor 17-thia-eburnamenine-14(15H)-one

STEP A: Methyl 5,5'-bis-[2-(3-indolyl)-ethyl]-4,4'-dioxo-7,7'-dithio-di-(5-aza-2-heptenoate)

(a) Preparation of acid chloride 7.5 ml of thionyl chloride were added to a solution of 6.77 g of (4) methyl 2-bromo-succinate acid and 67 ml of chloroform and refluxed for one hour. The chloroform and excess thionyl chloride were distilled off under reduced pressure to obtain 7 g of acid chloride which was used as is.

(b) Amidification 20 g of potassium carbonate in 60 ml of water, then 0.32 g of tetrabutylammonium bromide were added to a solution of 6.4 g of N,N'-bis-[2-(3-indolyl)-ethyl-2,2'-dithio diethanamine in 50 ml of chloroform. The above acid chloride in solution in 50 ml of chloroform was introduced over five minutes with strong stirring which was continued overnight at ambient temperature. The solution was decanted and the aqueous phase was extracted twice with 50 ml of chloroform. The organic phase was washed three times with 50 ml of water and which were extracted with 50 ml of chloroform. After drying the organic phase and concentration under reduced pressure, 11 g of an oil were obtained which was chromatographed on silica (eluant: ethyl acetate - methylene chloride 8:2) to obtain 7.3 g of the desired product in form of an oil with an Rf=0.75.

| Infra-red spectrum (CHCl$_3$) cm$^{-1}$ | |
|---|---|
| NH indole | 3478 |
| $>$C=O ester | 1724 |
| $>$C=O amide | 1622 |
| No SH band | |

STEP B: Methyl 4-[2-(3-indolyl)-ethyl]-3-oxo-2-thiomorpholinoacetate 70 ml of water were added to a solution of 7.3 g of the product of Step A in 140 ml of monoglyme and then 3.47 g of triphenylphosphine were introduced all at once. The mixture was stirred for 48 hours at ambient temperature and then 100 ml of ethyl acetate and 50 ml of water were added. The aqueous phase was extracted with 100 ml of ethyl acetate and the total organic solution was washed with 50 ml of water, dried over sodium sulfate and concentrated under reduced pressure to obtain 11 g of an oil which was chromatographed on silica (eluant: ethyl acetate - methylene chloride 8:2) to obtain 6.6 g of pure desired product melting at 120° C.

| Infra-red (CHCl$_3$) cm$^{-1}$ | |
|---|---|
| $>$C=O ester | 1737 |
| $>$C=O amide | 1657 |
| NH indole | 3479 |

STEP C: Methyl [1α, 12bβ(±)]-3,4,6,7,12,12b-hexahydro-1H-[1,4-thiazino]-[4',3',1,2]-pyrido[3,4-b]indol-1-acetate 1 g of the product of Step B was dissolved in 10 ml of phosphorus oxychloride and the mixture was heated to 80° C. and kept at this temperature for 3 hours. The mixture was concentrated under reduced pressure and the dry extract was dissolved in 50 ml of methanol. Then, 1 g of sodium borohydride was reacted at a temperature of 15°±5° C. and the suspension was concentrated under reduced pressure. The residue was taken up in 10 ml of ethyl acetate and 50 ml of water and the aqueous phase was decanted and extracted with 50 ml of ethyl acetate. The combined organic phases were washed three times with 25 ml of water and was then extracted with ethyl acetate. After drying over sodium sulfate and concentrating to dryness, 0.78 g of solid were obtained which was chromatographed on silica (eluant: methylene chloride - ethyl acetate 8:2) to obtain 0.51 g of pure desired product melting at 212° C.

| Infra-red (CHCl$_3$) cm$^{-1}$ | |
|---|---|
| No C=O lactam | |
| NH indole | 3464 |
| $>$C=O ester | 1727. |

STEP D: (±)-20,21-dinor-17-thia-eburnamenine-14(15H)-one 0.4 g of sodium methylate was added under a nitrogen atmosphere and at ambient temperature to a suspension of 1.2 g of the product of Step C in 48 ml of methanol and the mixture was refluxed for 7 hours. The methanol was distilled off under reduced pressure and the residue was taken up in a mixture of chloroform-methanol (2-1). The filtrate was concentrated under reduced pressure to obtain 0.9 g of a solid which was purified on silica and elution with methylene chloride - methanol (95-5) to obtain 0.65 g of the expected product melting at 220° C.

| Infra-red (CHCl$_3$) cm$^{-1}$ | |
|---|---|
| No NH | |
| $>$C=O | 1705 |
| C=C | 1636. |

EXAMPLE 2

Neutral fumarate of (±)-20,21-dinor-17-thia-eburnamenine-14(15H)-one 0.71 g of the product of Example 1 were dissolved in 90 ml of boiling ethanol and 0.29 g of fumaric acid in solution in 10 ml of boiling ethanol were added. The solution was cooled to 0° C. while stirring for 30 minutes and the product was filtered, washed with ethanol and dried under reduced pressure at 50° C. to obtain 0.71 g of the expected product melting at 250° C.

| Analysis: $C_{18}H_{18}N_2O_3S$; molecular weight = 342,419 | | | | |
|---|---|---|---|---|
| Calculated | % C 63.14 | % H 5.30 | % N 8.18 | % S 9.36 |
| Found: | 63.1 | 5.20 | 8.2 | 9.4 |

EXAMPLE 3

[16α(±)]-20,21-dinor-17-thia-eburnamenine-14(15H)-one

A solution of 6.5 g of the product of Step B of Example 1 in 65 ml of phosphorus oxychloride was heated for 4 hours at 80° C. and then was concentrated to dryness under reduced pressure. The solid residue was taken up in 65 ml of 5N hydrochloric acid and then heated overnight at 80° C. 65 ml of water were added to the suspension which was then cooled and stirred for 30 minutes at 0° C. and filtered. The salt formed was washed with water and product was suspended in 65 ml of acetic acid, then submitted to the action of 5.9 g of sodium borohydride at 15° C.±5° C. After 30 minutes of stirring, 130 ml of water were added and the solution was neutralized with 22° Be ammonia. The suspension was filtered, washed and dried under reduced pressure to obtain 4.75 g of a solid which was chromatographed on silica (eluant: methylene chloride - ethyl acetate 8:2) to obtain 3.36 g of the expected product melting at 180° C.

| Infra-red (CHCl$_3$) cm$^{-1}$ | |
|---|---|
| No NH | |
| C=O | 1709 |
| C=C | 1649. |

EXAMPLE 4

[16α(±)]-20,21-dinor-17-thia-eburnamenine-14(15H)-one hydrochloride 2.84 g of the product of Example 3 were dissolved in 400 ml of boiling methanol and 1 ml of pure 22° Be hydrochloric acid was added hot. The mixture was allowed to return to ambient temperature and stirring was maintained for 1 hour at −10° C. After filtration and drying, 2.57 g of the expected hydrochloride melting at 230° C. were obtained.

| Analysis: $C_{16}H_{16}N_2OS$, HCl; molecular weight = 320.843 | | | | | |
|---|---|---|---|---|---|
| Calculated: | % C 59.9 | % H 5.34 | % N 8.73 | % S 9.99 | % Cl 11.05 |
| Found: | 59.7 | 5.3 | 8.6 | 9.8 | 11.2 |

EXAMPLE 5

[14β,16α(±)]-14,15-dihydro-20,21-dinor-17-thia-eburnamenine-14-ol 4.1 g of the product of Example 3 were partially dissolved in 80 ml of tetrahydrofuran and 30.5 ml of sodium diethyl dihydro aluminate in toluene at 0.236 moles per 100 ml were added over 15 minutes at 0°–5° C. The mixture was stirred for 1 hour at 0° C. and then 40 ml of tetrahydrofuran with 20% water were added. Stirring was continued for 1 hour at ambient temperature and the precipitate formed was filtered and washed with tetrahydrofuran. The organic solution was concentrated under reduced pressure to obtain 4.5 g of a product which was a mixture of the 14α and 14β isomers. After chromatography on silica (eluant: methylene chloride - acetone (1-1), 1.5 g of the expected product were obtained melting at 220° C. and having a Rf=0.6. 1.23 g of the 14α product were also obtained (Rf=0.5) and 0.88 g of the 14α and 14β mixture.

| NMR Spectrum (DMSO, ppm) (14β) | |
|---|---|
| $>$CH—OH | 5.58 (dd: J = 5.5 and 9) |
| OH | 6.61 (d J = 9) |
| H$_5$ and H$_6$ | 7.06 |
| H$_4$ and H$_7$ | 7.40 (d) and 7.65 (d) |
| Other protons | 1.8 to 3.2 |

EXAMPLE 6

[14α,16α(±)-14,15-dihydro-20,21-dinor-17-thia-eburnamenine-14-ol 0.88 g of the 14α and 14β mixture of Example 5 were suspended in 10 ml of methanol and 10 ml of 5N sodium hydroxyde and the mixture was refluxed overnight. 20 ml of chilled water were added and the mixture was stirred for 15 minutes at 0°–5° C., then filtered and washed with water to obtain 0.800 g of the expected product which - with 1.23 g of the product obtained in Example 5 made a total of 2.03 g of 14α product melting at 265° C., Rf=0.5 (methylene chloride - acetone 1:1)

| NMR Spectrum (DMSO, ppm) 14α | |
|---|---|
| $>$CH—OH | 5.94 |
| OH | 6.33 (d) |
| H$_5$ and H$_6$ | 7.02 (t) and 7.09 (t) |
| H$_4$ and H$_7$ | 7.37 (d) and 7.44 (d) |
| Other protons | 1.9 to 3.4 |

EXAMPLE 7

[16α(±)]-20,21-dinor-17-thia-eburnamenine acid maleate 0.14 g of p-toluenesulfonic acid were added to a suspension of 2.8 g of the product of a 14α and 14β mixture as in Example 5 in 60 ml of anhydrous toluene and the mixture was refluxed overnight. 60 ml of ethyl acetate and 60 ml of water were added and the mixture was adjusted to an alkaline pH-value with 22° Be ammonia. The insoluble part was filtered off, and after decanting, the aqueous phase was extracted with ethyl acetate. The organic solution was washed with water, dried and concentration to dryness under reduced pressure to obtain 2 g of a product which was chromatographed on silica and eluted with methylene chloride - methanol 95:5 to obtain 1.28 g of the desired product in the form of a free base melting at 188° C.

Salification 1.28 g of the base product were dissolved in boiling ethyl acetate and 0.55 g of maleic acid dissolved in 10 ml of hot ethyl acetate were added. The solution was stirred for one hour at 0°–5° C. and the salt which crystallized was filtered off and dried under reduced pressure to obtain 1.67 g of the maleate melting at 174° C.

| Infra-red (CHCl₃) cm⁻¹ (on the free base) | |
|---|---|
| No OH | |
| —C=C— | 1648 |
| aromatics | 1615, 1565 |

EXAMPLE 8

[16α(±)]-14,15 dihydro-20,21-dinor-17-thia-eburnamenine acid maleate 30 ml of diisobutylaluminum hydride with 1 mole/l. in hexane were added all at once under a nitrogen atmosphere at ambient temperature to a solution of 1.5 g of the product of Example 3 in 30 ml of dry tetrahydrofuran with stirring for 4 hours at ambient temperature. 15 ml of a mixture of tetrahydrofuran - water 90:10 were added with stirring for 15 minutes at 0° C., followed by filtering the suspension. The precipitate was washed with a mixture of chloroform - methanol 2:1 and after evaporating to dryness, the residue was chromatographed on silica (eluant: methylene chloride - acetone 95:5) to obtain 0.7 g of white crystals of the free base melting at 138° C.

| Infra red spectrum (CHCl₃) cm⁻¹ | |
|---|---|
| No $>$C=O | |
| Aromatics | 1618 |
| —C=C— | 1480 |

Salification 0.128 g of maleic acid were added to a solution of 300 mg of the base in 10 ml of a mixture of ethyl acetate - ethanol 1:1 and the mixture was stirred for 90 minutes at ambient temperature, then filtered. The precipitate was washed with a mixture of ethyl acetate - ethanol 1:1, then dried to obtain 300 mg of the salified product in the form of crystals melting at 164° C.

EXAMPLE 9

[16α(±)]-20,21-dinor-17-thia-eburnamenine-14(15H)-one-17-oxide 1.02 g of hydrated magnesium perphthalate with 6 molecules of water in solution in 150 ml of water were added to a solution of 1 g of the product of Example 3 in 60 ml of hot ethanol. The mixture was heated for 2 hours at 50° C. and the ethanol was evaporated. The aqueous phase was alkalinized with sodium bicarbonate and the precipitated product was extracted with chloroform to obtain 900 mg of crude product which was chromatographed on silica and eluted with methylene chloride -methanol 9:1 to obtain 690 mg of the expected product melting at 240° C.

| Infra-red (CHCl₃) cm⁻¹ | |
|---|---|
| $>$C=O | 1709 |
| —C=C | 1649 |
| —S→O | 1058 |

EXAMPLE 10

[16α(±)]-20,21-dinor-17-thia-eburnamenine-14(15H)-one-17-oxide maleate 0.9 g of the base of Example 9 were dissolved by heating in a mixture of 50 ml of ethanol and 75 ml of ethyl acetate. 0.347 g of maleic acid in solution in 25 ml of hot ethyl acetate were added and the mixture was stirred for 20 minutes. The salt precipitated and stirring was continued for 2 hours at ambient temperature, followed by filtering and drying under reduced pressure to obtain 0.95 g of the expected product in the form of white crystals melting at 216° C.

Analysis: $C_{16}H_{16}N_2O_2S$, $C_4H_4O_4$; molecular weight = 416,455

| | % C | % H | % N | % S |
|---|---|---|---|---|
| Calculated: | 57.68 | 4.84 | 6.72 | 7.83 |
| Found: | 57.9 | 4.8 | 6.7 | 7.6 |

EXAMPLE 11

[14α, 16α(±)] 14,15-dihydro-20,21-dinor-17-thia-eburnamenine-14-ol-17-oxide and [14β, 16α(±)] 14,15-dihydro-20,21-dinor-17-thia-eburnamenine-14-ol-17-oxide 0.7 g of sodium borohydride were added in fractions to a solution of 1.4 g of the product of Example 9 in 200 ml of methanol with 10% of water and the mixture was refluxed for 4 hours. Then 0.7 g of sodium borohydride were added again and the mixture was stirred for one hour at reflux. The solvent was evaporated and the residue was taken up in 50 ml of methylene chloride. The organic solution was washed with 20 ml of water and then dried over sodium sulfate to obtain 1.4 g of crystals melting at 260° C. in the form of a mixture of 14α and 14β. The two isomers were separated by three successive chromatographies under weak pressure and elution with methylene chloride - methanol 95:5 to obtain 3 batches: 200 mg, then 400 mg of the 14α product and 600 mg of the 14β product. The two first batches were crystallized to obtain 0.328 g of pure 14α product melting at >260° C.

| NMR Spectrum (DMSO, ppm) | | |
|---|---|---|
| 14α | OH | 6.46 (d, J = 6 Hz) |
| —N—CH—CH₂<br>    \|<br>    OH | | 5.65 |
| 14β | OH | 6.68 (d, J = 9 Hz)<br>6.8 (d, J = 9 Hz) |
| —N—CH—CH₂<br>    \|<br>    OH | | 6.06 ppm |

EXAMPLE 12

[16α (±)] 20,21-dinor-17-thia-eburnamenine-17-oxide 0.066 g of p-toluene sulfonic acid were added to a suspension of 1.33 g of a mixture of the 14α and 14β isomers of Example 11 and the mixture was refluxed for 15 hours. The solution was cooled to 0° C. and alkalinized with 22° Be ammonia. The aqueous phase was extracted 3 times with 60 ml of ethyl acetate and the combined organic phases were washed with 30 ml of water and dried over sodium sulfate. After the solvent was evaporated, 1.8 g of product were obtained which was chromatographed on silica and eluted with methylene chloride - methanol 95:5 to obtain 0.95 g of the desired product as crystals melting at 220° C.

| NMR (CDCl₃, ppm) | |
|---|---|
| 3.65 (ddd J = 12-2.5 − 2 Hz) <br> 4.39 (dl J = 12 Hz) | angular H <br> 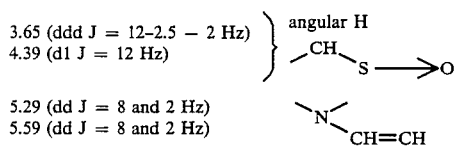 |
| 5.29 (dd J = 8 and 2 Hz) <br> 5.59 (dd J = 8 and 2 Hz) | >N−CH=CH |

EXAMPLE 13

[16α(±)] 20,21-dinor-17-thia-eburnamenine-17-oxide maleate 0.9 g of the base of Example 12 were dissolved in 180 ml of hot ethyl acetate and the hot solution was filtered. 0.387 g of maleic acid in solution in 4 ml of hot ethyl acetate were added and after 15 minutes of stirring at ambient temperature, the salt crystallized and was stirred for 3 hours at ambient temperature. The crystals were filtered and dried under reduced pressure at 60° C. to obtain 0.85 g of the expected salt melting at 178° C.

| NMR Spectrum (DMSO, ppm) | |
|---|---|
| 5.36 (dd J = 8 and 2 Hz) <br> 5.48 (dd J = 8 and 2 Hz) | >N−CH=CH− |
| 4.42 (dl J = 12 Hz) = | 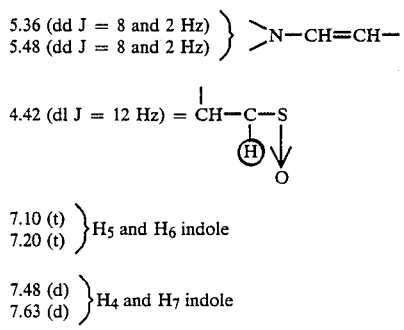 |
| 7.10 (t) <br> 7.20 (t) | H₅ and H₆ indole |
| 7.48 (d) <br> 7.63 (d) | H₄ and H₇ indole |

EXAMPLE 14

Pharmaceutical composition

Tablets of 50 mg of the product of Example 6 and sufficient excipient of lactose, talc, starch and magnesium stearate for a final weight of 350 mg were prepared.

Pharmaceutical Study

Mice hypobaric anoxemia test:

Batches of 10 mice were placed in a 2 liter chamber in which a depression of 620 mm Hg was realized over 55 seconds. The survival time was measured starting from the time $T_o$ and up to a maximum duration of 3 minutes. The products were administered intraperitoneally at a dose of 10 mg/kg and in a volume of 10 ml/kg, 60 minutes before the test. The following results were obtained, expressed as the percentage increase of survival time:

| Product of Example 2 | +16% |
|---|---|
| Product of Example 6 | +20% |

Various modifications of the products and method of the invention may be made without departing from the spirit or scope thereof and it is to be understood that the invention is intended to be limited only as defined in the appended claims.

What we claim is:

1. A compound selected from the group consisting of a compound of the formula

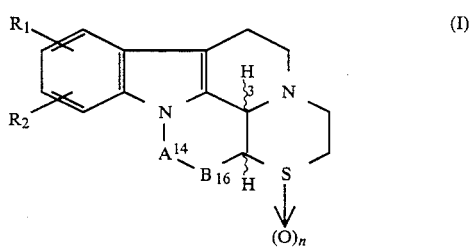

wherein R₁ and R₂ are individually selected from the group consisting of hydrogen, halogen, alkyl and alkoxy of 1 to 5 carbon atoms, hydroxy, trifluoromethyl and nitro, n is 0, 1 or 2 and the group:

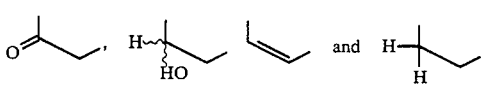 is selected from the group consisting of

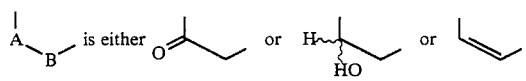

in all possible racemic or optically active isomer forms and their non-toxic, pharmaceutically acceptable acid addition salts.

2. A compound of claim 1 wherein R₁ and R₂ both are hydrogen and

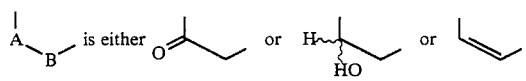

3. A compound of claim 1 selected from the group consisting of (±) 20,21-dinor-17-thia-eburnamenine-14(15H)-one and its non-toxic, pharmaceutically acceptable acid addition salts and (14α, 16α) (±) 14,15-dihydro-20,21-dinor-17-thia-eburnamenine-14-ol.

4. A process for the preparation of a compound of claim 1 comprising reacting a compound of the formula

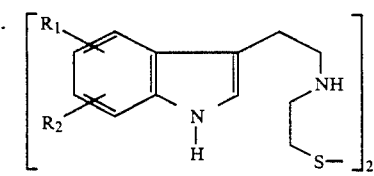

wherein R₁ and R₂ have the definition of claim 1 with an acid chloride of the formula

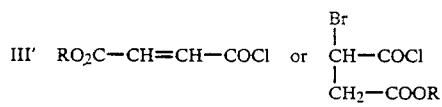

wherein R is alkyl of 1 to 2 carbon atoms to obtain a compound of the formula

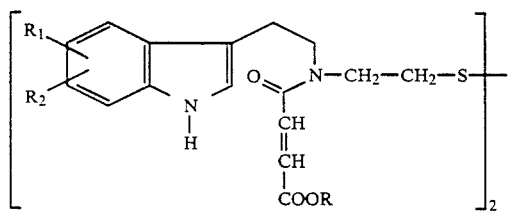

reacting the latter with a reducing agent to obtain a compound of the formula

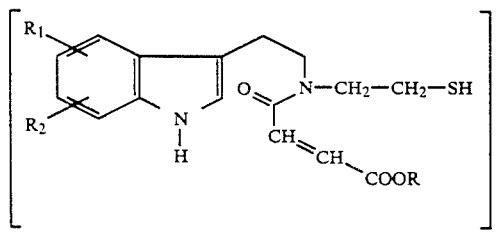

which cyclizes spontaneously into a compound of the formula

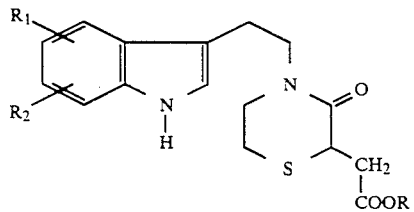

cyclizing the compound of formula V to form the salt of the formula

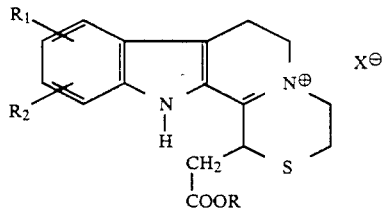

wherein X⊖ is a counter-ion and either reducing the salt of formula VI to obtain a compound of the formula in which the two hydrogens are in cis position

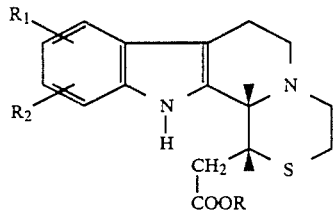

which product of formula VII is cyclized in a basic medium to obtain a compound of formula I in which

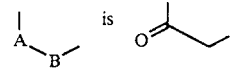 is 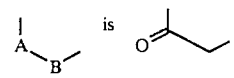

the 3- and 16- hydrogen atoms are in cis position with respect to each other, and n is equal to 0; or the salt of formula VI is cyclized to form a compound of the formula

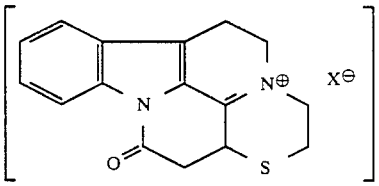

which compound is reduced to obtain a compound of formula I in which

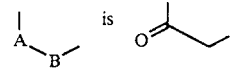 is 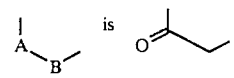

the 3- and 16- hydrogen atoms are in trans position with respect to each other and n is equal to 0 and the said products of formula I may be, if desired, reduced either into the corresponding compounds of formula I in which

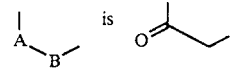 is 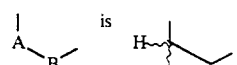

and n is equal to 0 or into compounds of formula I in which

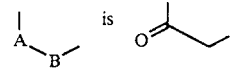 is 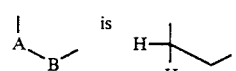

and n is equal to 0 and in that, if desired, the compounds of formula I are dehydrated to obtain the compounds of formula $I_{D1}$ and $I_{D2}$ representing the compounds of formula I in which

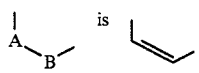 is and n is equal to 0, and in that, if desired, the compounds of formula I are submitted to the action of an oxidation agent to obtain the corresponding compounds in which n represents 1 or 2.

5. An analgesic composition comprising an analgesically effective amount of at least one compound of claim 1 and an inert pharmaceutical carrier.

6. A composition of claim 5 wherein $R_1$ and $R_2$ both are hydrogen and is either

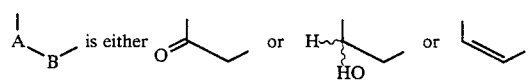

7. A composition of claim 5 wherein the active compound is selected from the group consisting of (±) 20,21-dinor-17-thia-eburnamenine-14(15H)-one and its non-toxic, pharmaceutically acceptable acid addition salts and (14α, 16α) (±) 14,15-dihydro-20,21-dinor-17-thia-eburnamenine-14-ol.

8. A method of relieving pain in warm-blooded animals comprising administering to warm-blooded animals an analgesically effective amount of at least one compound of claim 1.

9. A method of claim 8 wherein $R_1$ and $R_2$ both are hydrogen and is either

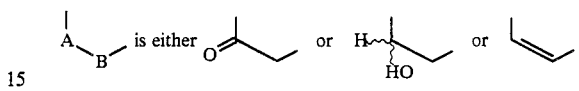

10. A method of claim 8 wherein the active compound is selected from the group consisting of (±) 20,21-dinor-17-thia-eburnamenine-14(15H)-one and its non-toxic, pharmaceutically acceptable acid addition salts and (14α, 16α) (±) 14,15-dihydro-14,15-dihydro-20,21-dinor-17-thia-eburnamenine-14-ol.

* * * * *